(12) United States Patent
Robertson et al.

(10) Patent No.: US 10,207,093 B2
(45) Date of Patent: Feb. 19, 2019

(54) MINIATURE INGESTIBLE DEVICE

(71) Applicant: Proteus Digital Health, Inc., Redwood City, CA (US)

(72) Inventors: Timothy Robertson, Belmont, CA (US); Hooman Hafezi, Redwood City, CA (US); Raymond Schmidt, San Francisco, CA (US)

(73) Assignee: PROTEUS DIGITAL HEALTH, INC., Redwood City, CA (US)

( * ) Notice: Subject to any disclaimer, the term of this patent is extended or adjusted under 35 U.S.C. 154(b) by 0 days.

(21) Appl. No.: 15/429,128

(22) Filed: Feb. 9, 2017

(65) Prior Publication Data

US 2017/0274194 A1  Sep. 28, 2017

Related U.S. Application Data

(63) Continuation of application No. 13/639,766, filed as application No. PCT/US2011/031536 on Apr. 7, 2011, now Pat. No. 9,597,487.
(Continued)

(51) Int. Cl.
*A61M 31/00* (2006.01)
*A61J 3/07* (2006.01)
*A61K 9/48* (2006.01)

(52) U.S. Cl.
CPC ............ *A61M 31/002* (2013.01); *A61J 3/07* (2013.01); *A61K 9/4808* (2013.01); *Y10T 156/10* (2015.01)

(58) Field of Classification Search
CPC ............... A61M 31/002; Y10T 156/10; Y10T 29/49117; A61K 9/4808; A61J 3/07;
(Continued)

(56) References Cited

U.S. PATENT DOCUMENTS

| 1,548,459 A | 8/1925 | Hammer |
| 2,587,158 A | 2/1952 | Hofberg |

(Continued)

FOREIGN PATENT DOCUMENTS

| CN | 1588649 | 3/2005 |
| CN | 1650844 | 8/2005 |

(Continued)

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.
(Continued)

*Primary Examiner* — Brian Wilson
(74) *Attorney, Agent, or Firm* — K&L Gates LLP

(57) ABSTRACT

The present invention discloses multiple approaches to preventing the capsule walls and other material from interfering with the performance of an electronic device once the device is activated by surrounding fluid. In accordance with the teachings of the present invention, a miniature ingestible device (MID) may be created using excipients and films. The MID, in accordance with various aspects of the present invention, will have a coating or laminating surrounding an electronic device and separating and isolating the device from the pharmaceutical product or drug within the capsule once the capsule is ingested as well as from the capsule itself as the capsule walls begin to collapse during the disintegration process.

6 Claims, 5 Drawing Sheets

Related U.S. Application Data

(60) Provisional application No. 61/416,150, filed on Nov. 22, 2010, provisional application No. 61/321,846, filed on Apr. 7, 2010.

(58) Field of Classification Search
CPC ... A61J 3/007; G06K 7/0013; G06K 7/10168; A61B 5/07; A61B 5/681; A61B 5/4833; A61B 5/6861; A61B 5/7282; A61B 5/1473; A61B 5/0028; A61B 5/0031; A61B 5/4839; A61B 5/073; A61B 2562/162; A61B 2562/08; A61B 2560/0214; A61B 2560/0462; H01Q 1/273; H04Q 5/22
USPC .......... 340/850, 852, 870.01, 539.12, 572.1, 340/572.7, 572.8, 573.1, 10.1, 340/10.4–10.42; 455/41.1, 41.2, 41.3; 600/302; 604/890.01
See application file for complete search history.

(56) References Cited

U.S. PATENT DOCUMENTS

| | | |
|---|---|---|
| 2,973,555 A | 3/1961 | Schwepke |
| 3,048,526 A | 8/1962 | Boswell |
| 3,079,824 A | 3/1963 | Schott |
| 3,096,248 A | 7/1963 | Rudzki |
| 3,176,399 A | 4/1965 | Marino et al. |
| 3,589,943 A | 6/1971 | Grubb et al. |
| 3,607,788 A | 9/1971 | Adolph |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,799,802 A | 3/1974 | Schneble, Jr. et al. |
| 3,828,766 A | 8/1974 | Krasnow |
| 3,837,339 A | 9/1974 | Aisenberg et al. |
| 3,849,041 A | 11/1974 | Knapp |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,139,589 A | 2/1979 | Beringer et al. |
| 4,143,770 A | 3/1979 | Grimmell et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,559,950 A | 12/1985 | Vaughan |
| 4,564,363 A | 1/1986 | Bagnall et al. |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,775,536 A | 10/1988 | Patell |
| 4,784,162 A | 11/1988 | Ricks |
| 4,793,825 A | 12/1988 | Benjamin et al. |
| 4,814,181 A | 3/1989 | Jordan et al. |
| 4,844,076 A | 7/1989 | Lesho |
| 4,847,090 A | 7/1989 | Della Posta et al. |
| 4,876,093 A | 10/1989 | Theeuwes et al. |
| 4,891,223 A | 1/1990 | Ambegaonakar et al. |
| 4,896,261 A | 1/1990 | Nolan |
| 4,900,552 A | 2/1990 | Sanvordeker et al. |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,018,335 A | 5/1991 | Yamamoto et al. |
| 5,079,006 A | 1/1992 | Urguhart |
| 5,110,441 A | 5/1992 | Kinlen et al. |
| 5,160,885 A | 11/1992 | Hannam et al. |
| 5,167,626 A | 12/1992 | Casper |
| 5,176,626 A | 1/1993 | Soehendra |
| 5,187,723 A | 2/1993 | Mueller |
| 5,213,738 A | 5/1993 | Hampton et al. |
| 5,218,343 A | 6/1993 | Stobbe et al. |
| 5,261,402 A | 11/1993 | DiSabito |
| 5,263,481 A | 11/1993 | Axelgaard et al. |
| 5,273,066 A | 12/1993 | Graham et al. |
| 5,279,607 A | 1/1994 | Schentag et al. |
| 5,281,287 A | 1/1994 | Lloyd |
| 5,283,136 A | 2/1994 | Peled et al. |
| 5,288,564 A | 2/1994 | Klein |
| 5,305,745 A | 4/1994 | Zacouto |
| 5,318,557 A | 6/1994 | Gross |
| 5,331,953 A | 7/1994 | Andersson et al. |
| 5,394,882 A | 3/1995 | Mawhinney |
| 5,395,366 A | 3/1995 | D'Andrea et al. |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,458,994 A | 10/1995 | Nesselbeck et al. |
| 5,485,841 A | 1/1996 | Watkin et al. |
| 5,506,248 A | 4/1996 | Nikfar et al. |
| 5,551,020 A | 8/1996 | Flax et al. |
| 5,567,210 A | 10/1996 | Bates et al. |
| 5,596,302 A | 1/1997 | Mastrocola et al. |
| 5,600,548 A | 2/1997 | Nguyen et al. |
| 5,603,363 A | 2/1997 | Nelson |
| 5,634,468 A | 6/1997 | Platt |
| 5,645,063 A | 7/1997 | Straka et al. |
| 5,659,247 A | 8/1997 | Clements |
| 5,703,463 A | 12/1997 | Smith |
| 5,705,189 A | 1/1998 | Lehmann et al. |
| 5,724,432 A | 3/1998 | Bouvet et al. |
| 5,738,708 A | 4/1998 | Peachey et al. |
| 5,740,811 A | 4/1998 | Hedberg |
| 5,757,326 A | 5/1998 | Koyama et al. |
| 5,772,575 A | 6/1998 | Lesinski et al. |
| 5,792,048 A | 8/1998 | Schaefer |
| 5,802,467 A | 9/1998 | Salazar |
| 5,833,716 A | 11/1998 | Bar-Or |
| 5,842,324 A | 12/1998 | Grosskopf et al. |
| 5,845,265 A | 12/1998 | Woolston |
| 5,862,803 A | 1/1999 | Besson |
| 5,868,136 A | 2/1999 | Fox |
| 5,914,132 A | 6/1999 | Kelm et al. |
| 5,914,701 A | 6/1999 | Gersheneld et al. |
| 5,925,030 A | 7/1999 | Gross et al. |
| 5,957,854 A | 9/1999 | Besson et al. |
| 5,963,132 A | 10/1999 | Yoakum et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,018,229 A | 1/2000 | Mitchell et al. |
| 6,038,464 A | 3/2000 | Axelgaard et al. |
| 6,042,710 A | 3/2000 | Dubrow |
| 6,047,203 A | 4/2000 | Sackner |
| 6,068,465 A | 5/2000 | Wilson |
| 6,068,589 A | 5/2000 | Neukermans |
| 6,076,016 A | 6/2000 | Feierbach et al. |

(56) References Cited

U.S. PATENT DOCUMENTS

| | | |
|---|---|---|
| 6,081,734 A | 6/2000 | Batz |
| 6,091,975 A | 7/2000 | Daddona et al. |
| 6,095,985 A | 8/2000 | Raymond et al. |
| 6,115,636 A | 9/2000 | Ryan |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,317,714 B1 | 11/2001 | Del Castillo |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Noehl et al. |
| 6,394,997 B1 | 5/2002 | Lemelson |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,496,705 B1 | 12/2002 | Ng et al. |
| 6,526,315 B1 | 2/2003 | Inagawa |
| 6,531,026 B1 | 3/2003 | Takeichi et al. |
| 6,544,174 B2 | 4/2003 | West |
| 6,547,994 B1 | 4/2003 | Monkhouse et al. |
| 6,564,079 B1 | 5/2003 | Cory |
| 6,567,685 B2 | 5/2003 | Takamori et al. |
| 6,572,636 B1 | 6/2003 | Hagen et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,602,518 B2 | 8/2003 | Seielstad et al. |
| 6,605,038 B1 | 8/2003 | Teller |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,767,200 B2 | 7/2004 | Sowden et al. |
| 6,773,429 B2 | 8/2004 | Sheppard et al. |
| 6,800,060 B2 | 10/2004 | Marshall |
| 6,801,137 B2 | 10/2004 | Eggers et al. |
| 6,816,794 B2 | 11/2004 | Alvi |
| 6,822,554 B2 | 11/2004 | Vrijens et al. |
| 6,824,512 B2 | 11/2004 | Warkentin et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,888,337 B2 | 5/2005 | Sawyers |
| 6,889,165 B2 | 5/2005 | Lind et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,946,156 B2 | 9/2005 | Bunick |
| 6,951,536 B2 | 10/2005 | Yokoi |
| 6,957,107 B2 | 10/2005 | Rogers et al. |
| 6,958,603 B2 | 10/2005 | Kondo |
| 6,960,617 B2 | 11/2005 | Omidian et al. |
| 6,968,153 B1 | 11/2005 | Heinonen |
| 6,977,511 B2 | 12/2005 | Patel et al. |
| 6,982,094 B2 | 1/2006 | Sowden |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,061,236 B2 | 6/2006 | Britton |
| 7,083,578 B2 | 8/2006 | Lewkowicz |
| 7,116,252 B2 | 10/2006 | Teraguchi |
| 7,118,531 B2 | 10/2006 | Krill |
| 7,122,143 B2 | 10/2006 | Sowden et al. |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,199 B2 | 3/2007 | Leung et al. |
| 7,188,767 B2 | 3/2007 | Penuela |
| 7,194,038 B1 | 3/2007 | Inkinen |
| 7,196,495 B1 | 3/2007 | Burcham |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |

(56) References Cited

U.S. PATENT DOCUMENTS

| | | |
|---|---|---|
| 7,311,665 B2 | 12/2007 | Hawthorne |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,247 B2 | 6/2008 | Welch et al. |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,442,164 B2 | 10/2008 | Berrang et al. |
| 7,443,290 B2 | 10/2008 | Takiguchi |
| 7,458,887 B2 | 12/2008 | Kurosawa |
| 7,469,838 B2 | 12/2008 | Brooks et al. |
| 7,471,665 B2 | 12/2008 | Perlman |
| 7,471,992 B2 | 12/2008 | Schmidt et al. |
| 7,492,128 B2 | 2/2009 | Shen |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,527,807 B2 | 5/2009 | Choi et al. |
| 7,537,590 B2 | 5/2009 | Santini, Jr. et al. |
| 7,539,533 B2 | 5/2009 | Tran |
| 7,542,878 B2 | 6/2009 | Nanikashvili |
| 7,547,278 B2 | 6/2009 | Miyazaki et al. |
| 7,551,590 B2 | 6/2009 | Haller |
| 7,554,452 B2 | 6/2009 | Cole |
| 7,558,620 B2 | 7/2009 | Ishibashi |
| 7,575,005 B2 | 8/2009 | Mumford |
| 7,616,111 B2 | 11/2009 | Covannon |
| 7,617,001 B2 | 11/2009 | Penner et al. |
| 7,626,387 B2 | 12/2009 | Adachi |
| 7,639,473 B2 | 12/2009 | Hsu et al. |
| 7,640,802 B2 | 1/2010 | King et al. |
| 7,645,262 B2 | 1/2010 | Greenberg et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,686,839 B2 | 3/2010 | Parker |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,756,587 B2 | 7/2010 | Penner et al. |
| 7,760,104 B2 | 7/2010 | Asp |
| 7,782,991 B2 | 8/2010 | Sobchak et al. |
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,881,799 B2 | 2/2011 | Greenberg et al. |
| 7,975,587 B2 | 7/2011 | Schneider |
| 7,978,064 B2 | 7/2011 | Zdeblick et al. |
| 7,983,189 B2 | 7/2011 | Bugenhagen |
| 8,036,731 B2 | 10/2011 | Kimchy et al. |
| 8,036,748 B2 | 10/2011 | Zdeblick et al. |
| 8,054,047 B2 | 11/2011 | Chen et al. |
| 8,054,140 B2 | 11/2011 | Fleming et al. |
| 8,055,334 B2 | 11/2011 | Savage et al. |
| 8,082,919 B2 | 12/2011 | Brunnberg et al. |
| 8,119,045 B2 | 2/2012 | Schmidt et al. |
| 8,131,376 B1 | 3/2012 | Faraji et al. |
| 8,177,611 B2 | 5/2012 | Kang |
| 8,185,191 B1 | 5/2012 | Shapiro et al. |
| 8,185,646 B2 | 5/2012 | Headley |
| 8,200,320 B2 | 6/2012 | Kovacs |
| 8,207,731 B2 | 6/2012 | Moskalenko |
| 8,224,596 B2 | 7/2012 | Agrawal et al. |
| 8,253,586 B1 | 8/2012 | Matak |
| 8,254,853 B2 | 8/2012 | Rofougaran |
| 8,271,146 B2 | 9/2012 | Heber et al. |
| 8,298,574 B2 | 10/2012 | Tsabari et al. |
| 8,343,068 B2 | 1/2013 | Najafi et al. |
| 8,374,698 B2 | 2/2013 | Ok et al. |
| 8,389,003 B2 | 3/2013 | Mintchev et al. |
| 8,404,275 B2 | 3/2013 | Habboushe |
| 8,425,492 B2 | 4/2013 | Herbert et al. |
| 8,443,214 B2 | 5/2013 | Lee et al. |
| 8,454,528 B2 | 6/2013 | Yuen et al. |
| 8,532,776 B2 | 9/2013 | Greenberg et al. |
| 8,540,633 B2 | 9/2013 | Hafezi et al. |
| 8,540,664 B2 | 9/2013 | Robertson et al. |
| 8,545,402 B2 | 10/2013 | Hafezi et al. |
| 8,547,248 B2 | 10/2013 | Zdeblick et al. |
| 8,558,563 B2 | 10/2013 | Zdeblick |
| 8,564,432 B2 | 10/2013 | Covannon et al. |
| 8,597,186 B2 | 12/2013 | Hafezi et al. |
| 8,634,838 B2 | 1/2014 | Hellwig et al. |
| 8,647,358 B2 | 2/2014 | Brister et al. |
| 8,660,645 B2 | 2/2014 | Stevenson et al. |
| 8,668,643 B2 | 3/2014 | Kinast |
| 8,685,451 B2 | 4/2014 | Toneguzzo et al. |
| 8,697,057 B2 | 4/2014 | Van Epps et al. |
| 8,698,006 B2 | 4/2014 | Bealka et al. |
| 8,721,540 B2 | 5/2014 | Hafezi et al. |
| 8,758,237 B2 | 6/2014 | Sherman et al. |
| 8,784,308 B2 | 7/2014 | Duck et al. |
| 8,802,183 B2 | 8/2014 | Frank et al. |
| 8,816,847 B2 | 8/2014 | Zdeblick et al. |
| 8,836,513 B2 | 9/2014 | Hafezi et al. |
| 8,838,217 B2 | 9/2014 | Myr |
| 8,908,943 B2 | 12/2014 | Berry et al. |
| 8,912,908 B2 | 12/2014 | Berkman et al. |
| 8,926,509 B2 | 1/2015 | Magar et al. |
| 8,932,221 B2 | 1/2015 | Colliou et al. |
| 8,951,234 B2 | 2/2015 | Hafezi et al. |
| 8,989,837 B2 | 3/2015 | Weinstein et al. |
| 9,031,658 B2 | 5/2015 | Chiao et al. |
| 9,088,168 B2 | 7/2015 | Mach et al. |
| 9,107,806 B2 | 8/2015 | Hafezi et al. |
| 9,119,554 B2 | 9/2015 | Robertson et al. |
| 9,119,918 B2 | 9/2015 | Robertson et al. |
| 9,149,423 B2 | 10/2015 | Duck et al. |
| 9,158,890 B2 | 10/2015 | Meredith et al. |
| 9,161,707 B2 | 10/2015 | Hafezi et al. |
| 9,189,941 B2 | 11/2015 | Eschelman et al. |
| 9,226,663 B2 | 1/2016 | Fei |
| 9,226,679 B2 | 1/2016 | Balda |
| 9,268,909 B2 | 2/2016 | Jani et al. |
| 9,270,025 B2 | 2/2016 | Robertson et al. |
| 9,271,897 B2 | 3/2016 | Costello et al. |
| 9,277,864 B2 | 3/2016 | Yang et al. |

(56) References Cited

U.S. PATENT DOCUMENTS

| | | |
|---|---|---|
| 9,320,455 B2 | 4/2016 | Hafezi et al. |
| 9,415,010 B2 | 8/2016 | Hafezi et al. |
| 9,433,371 B2 | 9/2016 | Hafezi et al. |
| 9,439,582 B2 | 9/2016 | Berkman et al. |
| 9,439,599 B2 | 9/2016 | Thompson et al. |
| 9,517,012 B2 | 12/2016 | Lane et al. |
| 9,597,010 B2 | 3/2017 | Thompson et al. |
| 9,597,487 B2 | 3/2017 | Robertson et al. |
| 9,599,679 B2 | 3/2017 | Taylor et al. |
| 9,649,066 B2 | 5/2017 | Zdeblick et al. |
| 9,681,842 B2 | 6/2017 | Zdeblick et al. |
| 9,741,975 B2 | 8/2017 | Laulicht et al. |
| 9,756,874 B2 | 9/2017 | Arne et al. |
| 9,962,107 B2 | 5/2018 | Frank et al. |
| 2001/0027331 A1 | 10/2001 | Thompson |
| 2001/0044588 A1 | 11/2001 | Mault |
| 2001/0051766 A1 | 12/2001 | Gazdinski |
| 2002/0002326 A1 | 1/2002 | Causey et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0128934 A1 | 9/2002 | Shaer |
| 2002/0132226 A1 | 9/2002 | Nair |
| 2002/0136744 A1 | 9/2002 | McGlynn et al. |
| 2002/0179921 A1 | 12/2002 | Cohn |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0017826 A1 | 1/2003 | Fishman et al. |
| 2003/0023150 A1 | 1/2003 | Yokoi et al. |
| 2003/0028226 A1 | 2/2003 | Thompson |
| 2003/0062551 A1 | 4/2003 | Chen et al. |
| 2003/0065536 A1 | 4/2003 | Hansen |
| 2003/0076179 A1 | 4/2003 | Branch et al. |
| 2003/0083559 A1 | 5/2003 | Thompson |
| 2003/0091625 A1* | 5/2003 | Hariharan ................ A61J 3/10 424/465 |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0219484 A1 | 11/2003 | Sowden et al. |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115507 A1 | 6/2004 | Potter et al. |
| 2004/0115517 A1 | 6/2004 | Fukada et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167465 A1 | 8/2004 | Mihai et al. |
| 2004/0167801 A1 | 8/2004 | Say et al. |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0259899 A1 | 12/2004 | Sanghvi et al. |
| 2004/0260154 A1 | 12/2004 | Sidelnik |
| 2005/0003074 A1 | 1/2005 | Brown et al. |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0208251 A1 | 9/2005 | Aisenbrey |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0279054 A1 | 12/2005 | Mauze et al. |
| 2005/0280539 A1 | 12/2005 | Pettus |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |

(56) References Cited

U.S. PATENT DOCUMENTS

| | | |
|---|---|---|
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122494 A1 | 6/2006 | Bouchoucha |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0000804 A1 | 1/2008 | Carey et al. |
| 2008/0014866 A1 | 1/2008 | Lipowshi |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1* | 11/2008 | Zdeblick ............ A61B 5/0031 340/572.1 |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |

(56) References Cited

U.S. PATENT DOCUMENTS

| | | |
|---|---|---|
| 2009/0034209 A1 | 2/2009 | Joo |
| 2009/0043171 A1 | 2/2009 | Rule |
| 2009/0047357 A1 | 2/2009 | Tomohira et al. |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0069724 A1 | 3/2009 | Otto et al. |
| 2009/0076343 A1 | 3/2009 | James |
| 2009/0076350 A1 | 3/2009 | Bly et al. |
| 2009/0082645 A1 * | 3/2009 | Hafezi .................. A61B 5/073 600/302 |
| 2009/0087483 A1 | 4/2009 | Sison |
| 2009/0088618 A1 | 4/2009 | Ameson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0124965 A1 | 5/2009 | Greenberg et al. |
| 2009/0131774 A1 | 5/2009 | Sweitzer |
| 2009/0135886 A1 | 5/2009 | Robertson et al. |
| 2009/0142853 A1 | 6/2009 | Warrington et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0171420 A1 | 7/2009 | Brown et al. |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0194747 A1 | 8/2009 | Zou et al. |
| 2009/0197068 A1 | 8/2009 | Yamaguchi et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0260212 A1 | 10/2009 | Schmett et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0287109 A1 | 11/2009 | Ferren et al. |
| 2009/0295548 A1 | 12/2009 | Ronkka |
| 2009/0296677 A1 | 12/2009 | Mahany |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0010330 A1 | 1/2010 | Rankers |
| 2010/0033324 A1 | 2/2010 | Shimizu et al. |
| 2010/0036269 A1 | 2/2010 | Ferren et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0168659 A1 | 7/2010 | Say et al. |
| 2010/0179398 A1 | 7/2010 | Say et al. |
| 2010/0185055 A1 * | 7/2010 | Robertson ............ A61B 5/0031 600/117 |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |

(56) References Cited

U.S. PATENT DOCUMENTS

| | | |
|---|---|---|
| 2010/0234914 A1 | 9/2010 | Shen |
| 2010/0239616 A1* | 9/2010 | Hafezi ................. A61B 5/073 424/400 |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0297640 A1 | 11/2010 | Kumar et al. |
| 2010/0298650 A1 | 11/2010 | Moon et al. |
| 2010/0298730 A1 | 11/2010 | Tarassenko et al. |
| 2010/0312188 A1 | 12/2010 | Robertson et al. |
| 2010/0312580 A1 | 12/2010 | Tarassenko et al. |
| 2011/0009715 A1 | 1/2011 | O'Reilly et al. |
| 2011/0077660 A1 | 3/2011 | Janik et al. |
| 2011/0124983 A1 | 5/2011 | Kroll et al. |
| 2011/0134906 A1 | 6/2011 | Garudadri et al. |
| 2011/0160549 A1 | 6/2011 | Saroka et al. |
| 2011/0224912 A1 | 9/2011 | Bhavaraju et al. |
| 2011/0230732 A1 | 9/2011 | Edman et al. |
| 2011/0270135 A1 | 11/2011 | Dooley et al. |
| 2012/0004520 A1 | 1/2012 | Whitworth et al. |
| 2012/0011699 A1 | 1/2012 | Hafezi et al. |
| 2012/0016231 A1 | 1/2012 | Westmoreland |
| 2012/0032816 A1 | 2/2012 | Cho et al. |
| 2012/0062371 A1 | 3/2012 | Radivojevic et al. |
| 2012/0071743 A1 | 3/2012 | Todorov et al. |
| 2012/0109112 A1 | 5/2012 | Strand et al. |
| 2012/0179004 A1 | 7/2012 | Roesicke et al. |
| 2012/0245043 A1 | 9/2012 | England |
| 2012/0299723 A1 | 11/2012 | Hafezi et al. |
| 2013/0129869 A1 | 5/2013 | Hafezi et al. |
| 2013/0129872 A1 | 5/2013 | Kruger |
| 2013/0171596 A1 | 7/2013 | French |
| 2013/0172690 A1 | 7/2013 | Arne et al. |
| 2013/0185228 A1 | 7/2013 | Dresner |
| 2013/0196012 A1 | 8/2013 | Dill |
| 2013/0199662 A1 | 8/2013 | Gebbink |
| 2013/0209877 A1 | 8/2013 | Kren et al. |
| 2013/0223028 A1 | 8/2013 | Arne et al. |
| 2013/0275296 A1 | 10/2013 | Tietzen et al. |
| 2014/0066734 A1 | 3/2014 | Zdeblick |
| 2014/0179221 A1 | 6/2014 | Whitworth et al. |
| 2014/0180202 A1 | 6/2014 | Zdeblick et al. |
| 2014/0280125 A1 | 9/2014 | Bhardwaj et al. |
| 2014/0308930 A1 | 10/2014 | Tran |
| 2014/0349256 A1 | 11/2014 | Connor |
| 2014/0374276 A1 | 12/2014 | Guthrie et al. |
| 2015/0017486 A1 | 1/2015 | Lai |
| 2015/0059922 A1 | 3/2015 | Thompson et al. |
| 2015/0080678 A1 | 3/2015 | Frank et al. |
| 2015/0080680 A1 | 3/2015 | Zdeblick et al. |
| 2015/0112243 A1 | 4/2015 | Hafezi et al. |
| 2015/0127737 A1 | 5/2015 | Thompson et al. |
| 2015/0127738 A1 | 5/2015 | Thompson et al. |
| 2015/0149375 A1 | 5/2015 | Thompson et al. |
| 2015/0150480 A1 | 6/2015 | Zdeblick et al. |
| 2015/0164746 A1 | 6/2015 | Costello et al. |
| 2015/0230729 A1 | 8/2015 | Zdeblick et al. |
| 2015/0248833 A1 | 9/2015 | Arne et al. |
| 2015/0352343 A1 | 12/2015 | Hafezi et al. |
| 2015/0361234 A1 | 12/2015 | Hafezi et al. |
| 2016/0033667 A1 | 2/2016 | Schmidt et al. |
| 2016/0345906 A1 | 12/2016 | Johnson et al. |
| 2016/0380708 A1 | 12/2016 | Dua et al. |
| 2017/0000179 A1 | 1/2017 | Cheng et al. |
| 2017/0014046 A1 | 1/2017 | Hafezi et al. |
| 2017/0020182 A1 | 1/2017 | Schmidt et al. |
| 2017/0216569 A1 | 8/2017 | Hafezi et al. |
| 2017/0265813 A1 | 9/2017 | Zdeblick et al. |
| 2017/0274194 A1 | 9/2017 | Robertson et al. |
| 2017/0296799 A1 | 10/2017 | Hafezi et al. |
| 2018/0026680 A1 | 1/2018 | Shirvani et al. |
| 2018/0110441 A1 | 4/2018 | Frank et al. |
| 2018/0184698 A1 | 7/2018 | Arne et al. |

FOREIGN PATENT DOCUMENTS

| | | |
|---|---|---|
| CN | 101795202 | 8/2010 |
| DE | 10313005 | 10/2004 |
| EP | 0344939 | 12/1989 |
| EP | 0526166 | 2/1993 |
| EP | 0981152 | 2/2000 |
| EP | 1246356 | 10/2002 |
| EP | 1534054 | 5/2005 |
| EP | 1702553 | 9/2006 |
| EP | 1244308 | 12/2007 |
| EP | 2143369 | 1/2010 |
| GB | 827762 | 2/1960 |
| JP | 61072712 | 4/1986 |
| JP | H01285247 | 11/1989 |
| JP | 05228128 | 9/1993 |
| JP | H11195415 | 7/1999 |
| JP | 2000506410 | 5/2000 |
| JP | 2002263185 | 9/2002 |
| JP | 2002282219 | 10/2002 |
| JP | 2003050867 | 2/2003 |
| JP | 2004313242 | 11/2004 |
| JP | 2005073886 | 3/2005 |
| JP | 2005087552 | 4/2005 |
| JP | 2005102959 | 4/2005 |
| JP | 2005124708 | 5/2005 |
| JP | 2005514966 | 5/2005 |
| JP | 2005304880 | 11/2005 |
| JP | 2005343515 | 12/2005 |
| JP | 20055332328 | 12/2005 |
| JP | 2006006377 | 1/2006 |
| JP | 2006509574 | 3/2006 |
| JP | 2007200739 | 8/2007 |
| JP | 2007313340 | 12/2007 |
| JP | 2009514870 | 4/2009 |
| JP | 2009528909 | 8/2009 |
| KR | 200600977523 | 7/2006 |
| TW | 200406192 | 5/2004 |
| TW | 200916136 | 4/2009 |
| WO | WO1988002237 | 4/1988 |
| WO | WO1992021307 | 12/1992 |
| WO | WO1993008734 | 5/1993 |
| WO | WO1993019667 | 10/1993 |
| WO | WO1994001165 | 1/1994 |
| WO | WO1997039963 | 10/1997 |
| WO | WO1998043537 | 10/1998 |
| WO | WO1999037290 | 7/1999 |
| WO | WO1999059465 | 11/1999 |
| WO | WO2000032474 | 6/2000 |
| WO | WO2000033246 | 6/2000 |
| WO | WO2001000085 | 1/2001 |
| WO | WO2001047466 | 7/2001 |
| WO | WO2001058236 | 8/2001 |
| WO | WO2001074011 | 10/2001 |
| WO | WO2001080731 | 11/2001 |
| WO | WO2002000920 | 1/2002 |
| WO | WO2002045489 | 6/2002 |
| WO | WO2002058330 | 7/2002 |
| WO | WO2002062276 | 8/2002 |
| WO | WO2002087681 | 11/2002 |
| WO | WO2002095351 | 11/2002 |
| WO | WO2003005877 | 1/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004066833 | 8/2004 |
| WO | WO2004066834 | 8/2004 |
| WO | WO2004066903 | 8/2004 |
| WO | WO2004068881 | 8/2004 |

(56) References Cited

FOREIGN PATENT DOCUMENTS

| WO | WO2004075032 | 9/2004 | | |
|---|---|---|---|---|
| WO | WO2004109316 | 12/2004 | | |
| WO | WO2005011237 | 2/2005 | | |
| WO | WO2005020023 | 3/2005 | | |
| WO | WO2005024687 | 3/2005 | | |
| WO | WO2005041438 | 5/2005 | | |
| WO | WO2005047837 | 5/2005 | | |
| WO | WO2005051166 | 6/2005 | | |
| WO | WO2005053517 | 6/2005 | | |
| WO | WO2005083621 | 9/2005 | | |
| WO | WO2005110238 | 11/2005 | | |
| WO | WO2005123569 | 12/2005 | | |
| WO | WO2006021932 | 3/2006 | | |
| WO | WO2006027586 | 3/2006 | | |
| WO | WO2006028347 | 3/2006 | | |
| WO | WO2006055892 | 5/2006 | | |
| WO | WO2006055956 | 5/2006 | | |
| WO | WO2006075016 | 7/2006 | | |
| WO | WO2006100620 | 9/2006 | | |
| WO | WO2006104843 | 10/2006 | | |
| WO | WO2006116718 | 11/2006 | | |
| WO | WO2006127355 | 11/2006 | | |
| WO | WO2007001724 | 1/2007 | | |
| WO | WO2007001742 | 1/2007 | | |
| WO | WO2007013952 | 2/2007 | | |
| WO | WO2007014084 | 2/2007 | | |
| WO | WO2007014527 | 2/2007 | | |
| WO | WO2007021496 | 2/2007 | | |
| WO | WO2007027660 | 3/2007 | | |
| WO | WO2007028035 | 3/2007 | | |
| WO | WO2007036687 | 4/2007 | | |
| WO | WO2007036741 | 4/2007 | | |
| WO | WO2007036746 | 4/2007 | | |
| WO | WO2007040878 | 4/2007 | | |
| WO | WO2007067054 | 6/2007 | | |
| WO | WO2007071180 | 6/2007 | | |
| WO | WO2007096810 | 8/2007 | | |
| WO | WO2007101141 | 9/2007 | | |
| WO | WO2007115087 | 10/2007 | | |
| WO | WO2007120946 | 10/2007 | | |
| WO | WO2007127316 | 11/2007 | | |
| WO | WO2007127879 | 11/2007 | | |
| WO | WO2007128165 | 11/2007 | | |
| WO | WO2007130491 | 11/2007 | | |
| WO | WO2007143535 | 12/2007 | | |
| WO | WO2007149546 | 12/2007 | | |
| WO | WO2008008281 | 1/2008 | | |
| WO | WO2008012700 | 1/2008 | | |
| WO | WO2008030482 | 3/2008 | | |
| WO | WO/2008/052136 | * 5/2008 | ............... | A61B 5/00 |
| WO | WO2008063626 | 5/2008 | | |
| WO | WO2008066617 | 6/2008 | | |
| WO | WO2008076464 | 6/2008 | | |
| WO | WO2008089232 | 7/2008 | | |
| WO | WO2008091683 | 7/2008 | | |
| WO | WO/2008/095183 | * 8/2008 | ............... | A61B 1/05 |
| WO | WO2008097652 | 8/2008 | | |
| WO | WO2008101107 | 8/2008 | | |
| WO | WO2008112577 | 9/2008 | | |
| WO | WO2008112578 | 9/2008 | | |
| WO | WO2008120156 | 10/2008 | | |
| WO | WO2008133394 | 11/2008 | | |
| WO | WO2008134185 | 11/2008 | | |
| WO | WO2008150633 | 12/2008 | | |
| WO | WO2009000447 | 12/2008 | | |
| WO | WO2009001108 | 12/2008 | | |
| WO | WO2009006615 | 1/2009 | | |
| WO | WO2009029453 | 3/2009 | | |
| WO | WO2009031149 | 3/2009 | | |
| WO | WO2009036334 | 3/2009 | | |
| WO | WO2009051829 | 4/2009 | | |
| WO | WO2009051830 | 4/2009 | | |
| WO | WO2009063377 | 5/2009 | | |
| WO | WO2009081348 | 7/2009 | | |
| WO | WO2009111664 | 9/2009 | | |
| WO | WO2009146082 | 12/2009 | | |
| WO | WO2010009100 | 1/2010 | | |
| WO | WO2010011833 | 1/2010 | | |
| WO | WO2010019778 | 2/2010 | | |
| WO | WO2010057049 | 5/2010 | | |
| WO | WO2010080765 | 7/2010 | | |
| WO | WO2010080843 | 7/2010 | | |
| WO | WO2010107563 | 9/2010 | | |
| WO | WO2010129288 | 11/2010 | | |
| WO | WO2010132331 | 11/2010 | | |
| WO | WO2010135516 | 11/2010 | | |
| WO | WO2011068963 | 6/2011 | | |
| WO | WO2011133799 | 10/2011 | | |
| WO | WO2011159336 | 12/2011 | | |
| WO | WO2011159337 | 12/2011 | | |
| WO | WO2011159338 | 12/2011 | | |
| WO | WO2011159339 | 12/2011 | | |
| WO | WO2012112561 | 8/2012 | | |
| WO | WO2015112603 | 7/2015 | | |
| WO | WO2015112604 | 7/2015 | | |
| WO | WO2015119911 | 8/2015 | | |

OTHER PUBLICATIONS

Arshak et al., A Review and Adaptation of Methods of Object Tracking to Telemetry Capsules IC-Med (2007) vol. 1, No. 1, Issue 1, 12pp.

"ASGE Technology Status Evaluation Report: wireless capsule endoscopy" American Soc. for Gastrointestinal Endoscopy (2006) vol. 63, No. 4; 7 pp.

Au-Yeung, K., et al., "A Networked System for Self-Management of Drug Therapy and Wellness", Wireless Health '10, Oct. 5-7, 2010, San Diego, 9 pages.

Aydin et al., "Design and implementation considerations for an advanced wireless interface in miniaturized integrated sensor Microsystems" Sch. of Eng. & Electron., Edinburgh Univ., UK; (2003); abstract (1 page).

Barrie, Heidelberg pH capsule gastric analysis. Texbook of Natural Medicine, (1992), Pizzorno, Murray & Barrie (4 pages).

Bohidar et al., "Dielectric Behavior of Gelatin Solutions and Gels" Colloid Polym Sci (1998) 276:81-86.

Brock, "Smart Medicine: The Application of Auto-ID Technology to Healthcare" Auto-ID Labs (2002) http://www.autoidlabs.org/uploads/media/MIT-AUTOID-WH-010.pdf (14 pages).

Carlson et al., "Evaluation of a non-invasive respiratory monitoring system for sleeping subjects" Physiological Measurement (1999) 20(1): 53.

Coury, L. "Conductance Measurement Part 1: Theory"; Current Separations, 18:3 (1999) p. 91-96.

Delvaux et al., "Capsule endoscopy: Technique and indications" Clinical Gastroenterology (2008) vol. 22, Issue 5, pp. 813-837.

Description of ePatch Technology Platform for ECG and EMG, located it http://www.madebydelta.com/imported/images/DELTA_Web/documents/ME/ePatch_ECG_EMG.pdf, Dated Sep. 2, 2010; 1 page.

Dhar et al., "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf (5 pages).

Ferguson et al., "Dielectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Gaglani S. "Put Your Phone, or Skin, on Vibrate" MedGadget (2012) http://medgadget.com/2012/03/put-your-phone-or-skin-on-vibrate.html 8pp.

(56) References Cited

OTHER PUBLICATIONS

Gilson, D.R. "Molecular dynamics simulation of dipole interactions", Department of Physics, Hull University, Dec. (2002), p. 1-43.

Given Imaging, "Agile Patency Brochure" (2006) http://www.inclino.no/documents/AgilePatencyBrochure_Global_GMB-0118-01.pdf; 4pp.

Gonzalez-Guillaumin et al., "Ingestible capsule for impedance and pH monitoring in the esophagus" IEEE Trans Biomed Eng. (2007) 54(12): 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html (1 page).

Heydari et al., "Analysis of the PLL jitter due to power/ground and substrate noise"; IEEE Transactions on Circuits and Systems (2004) 51(12): 2404-16.

Hoeksma, J. "New 'smart pill' to track adherence" E-Health-Insider (2010) http://www.e-health-insider.com/news/5910/new_'smart_pill'_monitors_medicines (1 page).

Hoover et al., "Rx for health: Engineers design pill that signals it has been swallowed" University of Florida News (2010) 2pp.; http://news.ufl.edu/2010/03/31/antenna-pill-2/.

Intromedic, MicroCam Innovative Capsule Endoscope Pamphlet. (2006) 8 pp (http://www.intromedic.com/en/product/productinfo.asp) (8 pages).

ISFET—Ion Sensitive Field-Effect Transistor; Microsens S.A. pdf document. First cited in Office Action dated Jun. 13, 2011 for U.S. Appl. No. 12/238,345; 4pp.

Jung, S. "Dissolvable 'Transient Electronics' Will Be Good for Your Body and the Environment" MedGadget; Oct. 1, 2012; Online website: http://medgadget.com/2012/10/dissolvable-transient-electronics-will-be-good-for-your-body-and-the-environment.html; downloaded Oct. 24, 2012; 4 pp.

Juvenile Diabetes Research Foundation International (JDRF), "Artificial Pancreas Project" (2010); http://www.artificialpancreasproject.com/; 3 pp.

Kamada K., "Electrophoretic deposition assisted by soluble anode" Materials Letters 57 (2003) 2348-2351.

Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.

Kim et al., "A Semi-Interpenetrating Network System for a Polymer Membrane"; Eur. Polym. J. vol. 33 No. 7; pp. 1009-1014 (1997).

Li, P-Y, et al. "An electrochemical intraocular drug delivery device", Sensors and Actuators A 143 (2008) p. 41-48.

Lifescan, "OneTouch UltraLink™" http://www.lifescan.com/products/meters/ultralink (2010) 2 pp.

Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.

Mackay et al., "Endoradiosonde" Nature, (1957) 1239-1240, 179 Nature Publishing Group.

McKenzie et al., "Validation of a new telemetric core temperature monitor" J. Therm. Biol. (2004) 29(7-8):605-11.

Medtronic, "CareLink Therapy Management Software for Diabetes" (2010); https://carelink.minimed.com/patient/entry.jsp?bhcp=1; 1 pp.

Medtronic, "Carelink™ USB" (2008) http://www.medtronicdiabetes.com/pdf/carelink_usb_factsheet.pdf 2pp.

Medtronic "The New MiniMed Paradigm® REAL-Time Revel™ System" (2010) http://www.medtronicdiabetes.com/products/index.html; 2 pp.

Medtronic, "MINI MED Paradigm® Revel ™ Insulin Pump" (2010) http://www.medtronicdiabetes.com/products/insulinpumps/index.html; 2 pp.

Medtronic, Mini Med Paradigm™ Veo™ System: Factsheet (2010). http://www.medtronic-diabetes.com.au/downloads/Paradigm%20Veo%20Factsheet.pdf ; 4 pp.

Melanson, "Walkers swallow RFID pills for science" Engadget (2008); http://www.engadget.com/2008/07/29/walkers-swallow-rfid-pills-for-science/ (1 page).

Minimitter Co. Inc. "Actiheart" Traditional 510(k) Summary. Sep. 27, 2005 (8 pages).

Minimitter Co. Inc. Noninvasive technology to help your studies succeed. Mini Mitter.com Mar. 31, 2009 (4 pages).

Mini Mitter Co, Inc. 510(k) Premarket Notification Mini-Logger for Diagnostic Spirometer. 9-21 (1999) (9 pages).

Mini Mitter Co, Inc. 510(k) Premarket Notification for VitalSense. Apr. 22, 2004 (11 pages).

Minimitter Co. Inc. VitalSense Integrated Physiological Monitoring System. Product Description. (2005) (4 pages).

Minimitter Co. Inc. VitalSense Wireless Vital Signs Monitoring. Temperatures.com Mar. 31, 2009 (3 pages).

Mojaverian et al., "Estimation of gastric residence time of the Heidelberg capsule in humans: effect of varying food composition" Gastroenterology (1985) 89:(2): 392-7.

O'Brien et al., "The Production and Characterization of Chemically Reactive Porous Coatings of Zirconium Via Unbalanced Magnetron Sputtering" Surface and Coatings Technology (1996) 86-87; 200-206.

Park, "Medtronic to Buy MiniMed for $3.7 Billion" (2001) HomeCare; http://homecaremag.com/mag/medical_medtronic_buy_minimed/; 2 pp.

Philips Respironics Products, Noninvasive Technology to Help Your Studies Succeed. 510 (k) Permanent Notification for Vital Sense. Apr. 22, 2004; http/minimitter.com/products.cfm.

Radio Antennae, http://www.erikdeman.de/html/sail018h.htm; (2008) 5 pages.

"RFID "pill" monitors marchers" RFID News (2008) http://www.rfidnews.org/2008/07/23/rfid-pill-monitors-marchers/ (4 pages).

Rolison et al., "Electrically conductive oxide aerogels: new materials in electrochemistry" J. Mater. Chem. (2001) 1, 963-980.

Roulstone, et al., "Studies on Polymer Latex Films: I. A study of latex film morphology" Polymer International 24 (1991) pp. 87-94.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

Santini, J.T. et al, "Microchips as controlled drug delivery-devices", Agnew. Chem. Int. Ed. (2000), vol. 39, p. 2396-2407.

"SensiVida minimally invasive clinical systems" Investor Presentation Oct. 2009 28pp; http://www.sensividamedtech.com/SensiVidaGeneralOctober09.pdf; pp. 1-28.

Shawgo, R.S. et al. "BioMEMS from drug delivery", Current Opinion in Solid State and Material Science 6 (2002), p. 329-334.

Shin et al., "A Simple Route to Metal Nanodots and Nanoporous Metal Films"; Nano Letters, vol. 2, No. 9 (2002) pp. 933-936.

Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010); pp. 11-12.

"Smartlife awarded patent for knitted transducer" Innovation in Textiles News: http://www.innovationintextiles.com/articles/208.php; 2pp. (2009).

"The SmartPill Wireless Motility Capsule" Smartpill, The Measure of GI Health; (2010) http://www.smartpillcorp.com/index.cfm?pagepath=Products/The_SmartPill_Capsule&id=17814 (1 page).

Solanas et al., "RFID Technology for the Health Care Sector" Recent Patents on Electrical Engineering (2008) 1, 22-31.

Soper, S.A. et al. "Bio-Mems Technologies and Applications", Chapter 12, "MEMS for Drug Delivery", p. 325-346 (2007).

Swedberg, "University Team Sees Ingestible RFID Tag as a Boon to Clinical Trials" RFID Journal (2010) Apr. 27th; http://www.rfidjournal.com/article/view/7560/1 3pp.

Tajalli et al., "Improving the power-delay performance in subthreshold source-coupled logic circuits" Integrated Circuit and System

(56) References Cited

OTHER PUBLICATIONS

Design. Power and Timing Modeling, Optimization and Simulation, Springer Berlin Heidelberg (2008) 21-30.

Target Innovations, Tablet Metal Detector, https ://web. arch ive. org/web/20 130215063351 /http://www.metaldetectorindia.com/tablet -metal-detector. html, Feb. 15, 2013.

TargetPharmaceutical Metal Detector, Feb. 15, 2013 downloaded from Target Innovations, Tablet Metal Detector, Feb. 15, 2013.

Tatbul et al., "Confidence-based data management for personal area sensor networks" ACM International Conference Proceeding Series (2004) 72; 3 pages.

Tierney, M.J. et al "Electroreleasing Composite Membranes for Delivery of Insulin and other Biomacromolecules", J. Electrochem. Soc., vol. 137, No. 6, Jun. (1990), p. 2005-2006.

Trutag Technologies, Inc., Spectral Microtags for Authentication and Anti-Counterfeiting; "Product Authentication and Brand Protection Solutions"; http://www.trutags.com/; downloaded Feb. 12, 2013; 1 pp.

Walkey, "MOSFET Structure and Processing"; 97.398* Physical Electronics Lecture 20; 24 pages, First cited in Office Action dated Jun. 13, 2011 for U.S. Appl. No. 12/238,345.

Wang, X. et al "Resistance to Tracking and Erosion of Silicone Rubber Material under Various Types of Precipitation", Jpn. J. Appl. Phys. vol. 38 (1999) pp. 5170-5175.

Watson, et al., "Determination of the relationship between the pH and conductivity of gastric juice" Physiol Meas. 17 (1996) pp. 21-27.

Winter, J. et al. "The material properties of gelatin gels"; USA Ballistic Research Laboratories, Mar. 1975, p. 1-157.

Wongmanerod et al., "Determination of pore size distribution and surface area of thin porous silicon layers by spectroscopic ellipsometry" Applied Surface Science 172 (2001) 117-125.

Xiaoming et al., "A telemedicine system for wireless home healthcare based on bluetooth and the internet" Telemedicine Journal and e-health (2004) 10(S2): S110-6.

Yang et al., "Fast-switching frequency synthesizer with a discriminator-aided phase detector" IEEE Journal of Solid-State Circuits (2000) 35(10): 1445-52.

Yao et al., "Low Power Digital Communication in Implantable Devices Using Volume Conduction of Biological Tissues" Proceedings of the 28th IEEE, EMBS Annual International Conference, Aug. 30-Sep. 3, 2006; pp. 6249-6252.

Youtube video Pharmaceutical Metal Detector/Tablet Metal Detector/ Capsule Metal Detector/ Dry Fruits; https://www.youtube.com/watch?v=10126txam_s, May 12, 2012.

Zimmerman, "Personal Area Networks: Near-field intrabody communication" IBM Systems Journal (1996) 35 (3-4):609-17.

Zworykin, "A Radio Pill" Nature, (1957) 898, 179 Nature Publishing Group.

* cited by examiner

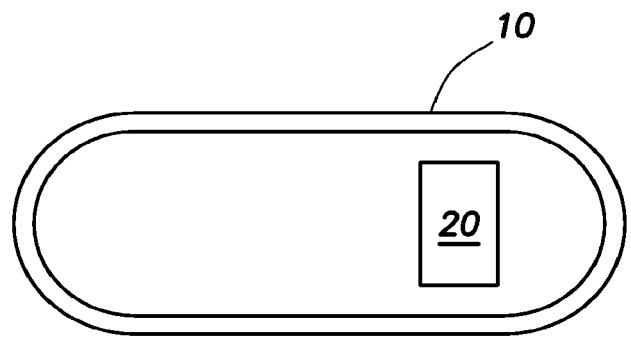
FIG.3
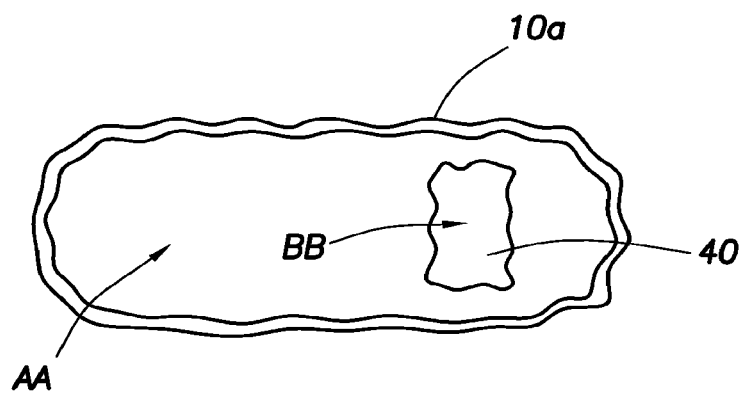
FIG.4
FIG.5
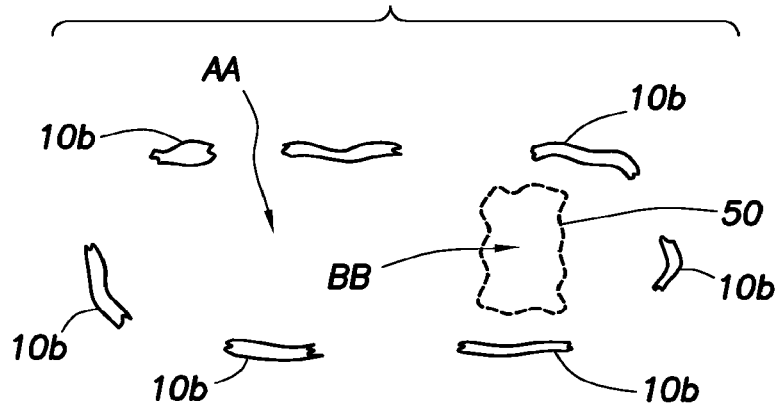

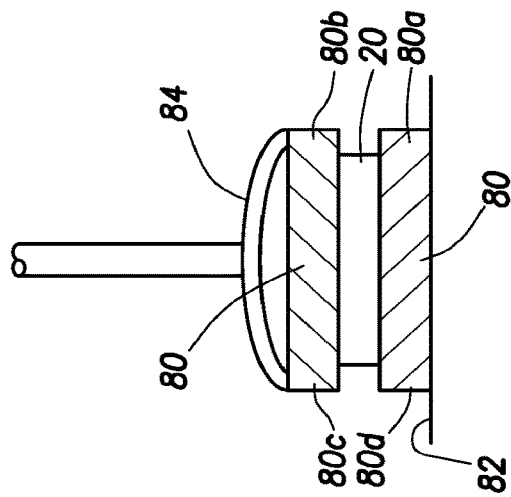
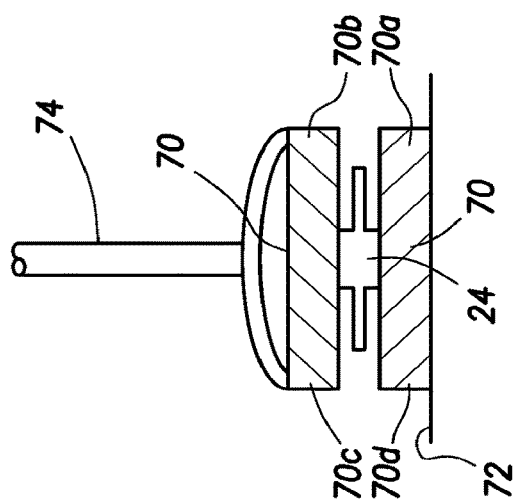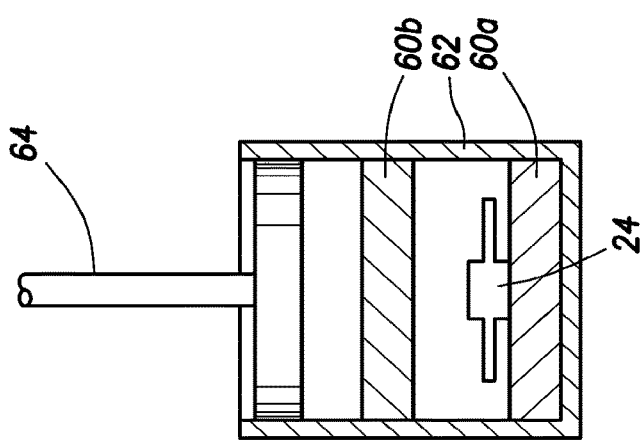

MINIATURE INGESTIBLE DEVICE

RELATED APPLICATIONS

This application is a continuation application claiming priority under 35 U.S.C. § 120 to U.S. patent application Ser. No. 13/639,766, titled MINIATURE INGESTIBLE DEVICE, which is a U.S. National Stage Application, filed under 35 U.S.C. § 371, of International Patent Application No. PCT/US2011/031536, filed Apr. 7, 2011 and titled MINIATURE INGESTIABLE DEVICE, which application, pursuant to 35 U.S.C. § 119(e), claims priority to the filing dates of U.S. Provisional Patent Application Ser. No. 61/321,846 filed on Apr. 7, 2010 entitled MINIATURE INGESTIBLE EVENT MARKER IN TABLET, and U.S. Provisional Patent Application Ser. No. 61/416,150 filed on Nov. 22, 2010 entitled INGESTIBLE DEVICE WITH PHARMACEUTICAL PRODUCT, the disclosures of which applications are herein incorporated by reference.

This application is related to and incorporates the following applications, including content incorporated therein, by reference: (A) U.S. patent application Ser. No. 12/564,017 entitled COMMUNICATION SYSTEM WITH PARTIAL POWER SOURCE and filed on Sep. 21, 2009 and published as US-2010/0081894; (B) U.S. Application number PCT/US12/447,172 filed on Oct. 25, 2007 and titled "CONTROLLED ACTIVATION INGESTIBLE IDENTIFIER." and published as US-2010-0239616.

FIELD OF INVENTION

The present invention relates to electronic devices and, more specifically, to electronic devices for use with a pharmaceutical product.

BACKGROUND

Capsules are made of a material that becomes gel-like once in contact with fluids. Such gel-like materials can interfere with the operation of an ingestible device that relies upon contact with the surrounding fluid when the device is carried inside the capsule. For example, gelatinous materials have low conductivity and, hence, if the device operates using conduction through fluids, then it will not operate properly. Thus, it is important to prevent the gel-like material of the capsule, as it is disintegrating, from coming into contact with the device's components.

Additionally, capsules contain pharmaceutical materials that can interact with or damage the device. For example, as the capsule disintegrated, the pharmaceutical material will dissolve into the surrounding fluid and change the chemical composition of the fluid immediately surrounding the pharmaceutical material and the change may prevent the device from operating optimally. The content of the capsule may include material, such as a drug or excipient or compound, that when dissolved at high concentrations, will interfere with the operation of the ingested device placed within the same capsule. As the material enters the solution at the site where the capsule is dissolving, there is a high concentration localized around the device. The stomach motion and diffusion disperses the capsule content throughout the stomach and reduces the concentration. During this time, the device will not operate properly optimally if activated in the localized high concentration areas.

Also, during long term storage the pharmaceutical material may begin to interact with the device and prevent optimal performance when the device is activated. For example, the product inside the capsule may be acidic and harmful to the electronic components. Alternatively, the content may be too basic, which can also harm the electronics. Furthermore, the material or product within the capsule will start to interact with the surrounding fluids, once the capsule is ingested and the capsule starts to disintegrate.

Therefore, what is needed is a device that is manufactured and assembled, such that the capsule walls or other materials present in the fluid environment immediately surrounding the device do not interfere with optimal performance of the device.

SUMMARY

The present invention discloses multiple approaches to preventing the capsule walls and other material from interfering with the performance of a device once the device is activated by surrounding fluid.

DESCRIPTION OF THE DRAWINGS

FIG. 3 shows a capsule containing a miniature ingestible device and an active agent prior to coming in contact with a fluid.

FIG. 4 shows the capsule of FIG. 3 at the initial stage on contacting the fluid with the walls of the capsule beginning to collapse and the miniature ingestible device in accordance with the present invention.

FIG. 5 shows the capsule of FIG. 4 at a more advanced stage of being in contact with the fluid in accordance with the present invention.

FIG. 6 shows an assembly unit for creating a miniature ingestible device in accordance with the present invention.

FIG. 7 shows an assembly unit for creating a miniature ingestible device in accordance with the present invention.

FIG. 8 shows an assembly unit for creating a miniature ingestible device in accordance with the present invention.

DETAILED DESCRIPTION

In accordance with the teachings of the present invention, a miniature ingestible device (MID) may be created using excipients and films. In accordance with the various aspects of the present invention, an ingestible event marker (or an ionic emission module, herein "IEM") such as the one disclosed in U.S. patent application Ser. No. 12/564,017, entitled COMMUNICATION SYSTEM WITH PARTIAL POWER SOURCE and filed on Sep. 21, 2009, may be covered with a disintegrating or a super-disintegrating material and/or a disintegrating film using various methods of manufacture to produce the MID. The MID, in accordance with various aspects of the present invention, may have a coating or lamination surrounding the IEM and separating and isolating the IEM from the pharmaceutical product or drug within the capsule once the capsule is ingested as well as from the capsule itself as the capsule walls begin to collapse during the disintegration process. In various aspects, the MID or device can be co-encapsulated with an active agent in a gel capsule, or other capsule or carrier. The subject compositions include an active agent/carrier component. The term "active agent" refers to a composition, which may be a solid or fluid, e.g., liquid, which has an amount of active agent, e.g., a dosage, present in a pharmaceutically acceptable carrier. The active agent may comprise, for example, a pharmaceutical product such as a tablet, capsule, softgel, powder, and other medicament forms.

Figure 1:
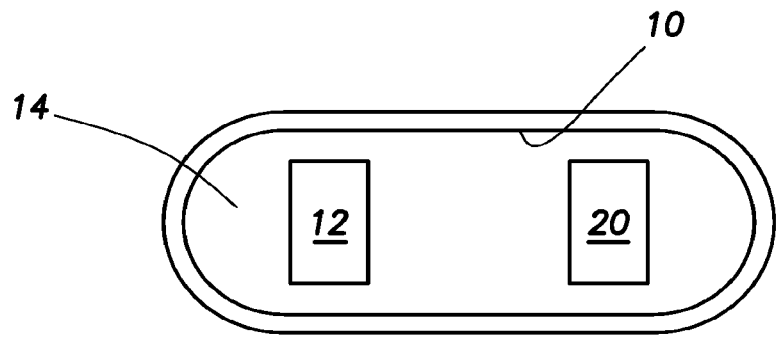
FIG. 1 shows a capsule containing a miniature ingestible device and an active agent in accordance with the present invention.

Referring now to FIG. 1, a capsule 10 includes a product 12 with a cavity 14. As understood in accordance with the present invention, the product 12 may be any pharmaceutical product or active agent. Also within the cavity 14 of the capsule 10 is a miniature ingestible device (MID) 20. The cavity 14 may also be filled with any excipient or product, in accordance with the teaching of the present invention. The capsule 10 is made of a dissolvable/disintegrating material, such as gelatin or hydroxypropyl methylcellulose (HPMC) material. Upon ingestion and contact with fluid, the walls of the capsule 10 turn into a soft gel-like material, due to contact with fluids.

Figure 2A:
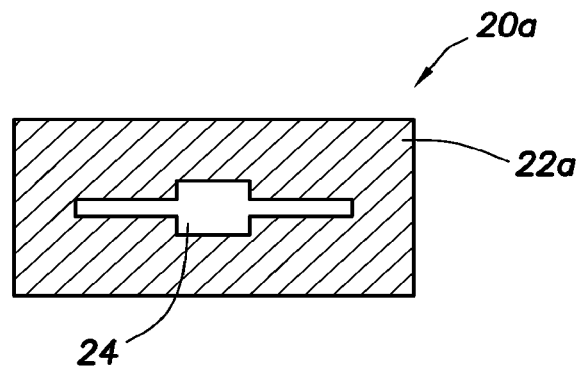
FIG. 2A shows a miniature ingestible device with a powder excipient in miniature tablet form in accordance with one aspect of the present invention.

Referring now to FIG. 2A, in accordance with one aspect of the present invention, a MID 20a is shown with an excipient material 22a surrounding an IEM 24. The scope of the present invention is not limited by the type of electronic device positioned within the excipient material 22a. Any electronic device may be used. Furthermore, the scope of the present invention is not limited by the type of excipient material used. For example, in accordance with one aspect of the present invention, the excipient material 22a may be a disintegrating material or a super disintegrating material. Example of materials include, but are not limited to, crospovidone disintegrants (e.g., Kollidon® disintegrants from BASF), polyvinyl polymer distintegrants, (e.g., Polyplasdone® disintegrants), croscarmellose sodium disintegrants (e.g., Ac-Di-Sol® distintegrants), sodium starch glycolates (e.g., Primojel® disintegrants, Explotab® disintegrants, and Vivastar® disintegrants), povidone, starch, and microcrystalline cellulose cellulose.

The MID 20a, in accordance with another aspect of the present invention, may be coated with a soluble polymer or film, such as HPMC or hydro hydroxypropyl cellulose (HPC) or blends thereof, whose function is to further delay the dissolution or disintegration of the tablet to allow for a delayed or timed separation of the IEM 24 from the capsule, such as capsule 10 of FIG. 1. Examples of the film materials may include any one or combination of the following: HPC, polyethylene oxide (PEO), forms of sugar such as sucrose or dextrose, sugar-alcohol such as Mannitol or Zylitol. To the film material additional materials may be added, including any one or combination of the following: plasticizer and/or salt, which includes sodium, potassium chloride, or any edible salt compound. Thus, in accordance with various aspects of the present invention, examples of the film materials include, but is not limited to: a combination of HPC and plasticizer with any one of PEO, sugar, or sugar-alcohol; a combination of HPC and plasticizer, a combination of PEO and plasticizer, and any of the foregoing combinations with salt. The scope of the present invention is not limited by the exact chemical composition of the film material and any combination of the above may be used to produce the film material as discussed in the present invention.

Figure 2B:
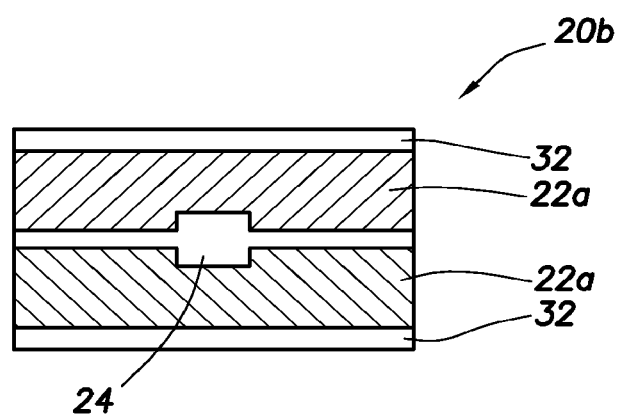
FIG. 2B shows a miniature ingestible device with a film and powder in the form of a miniature tablet in accordance with one aspect of the present invention

Referring now to FIG. 2B, in accordance with another aspect of the present invention, an MID 20b is shown with the excipient material 22a surrounding the IEM 24. Furthermore, the MID 20b includes a film material 32 positioned on the top surface and bottom surface of MID 20b and physically in contact with or laminated to the excipient material 22a. In accordance with another aspect of the present invention, the film material 32 is soluble and disintegrates upon contact with fluid. In accordance with another aspect of the present invention, the film material 32 does not disintegrate upon contact with fluid. The MID 20b is manufactured such that the excipient material 22a is exposed on the ends as shown, in accordance with another aspect of the present invention.

Figure 2C:
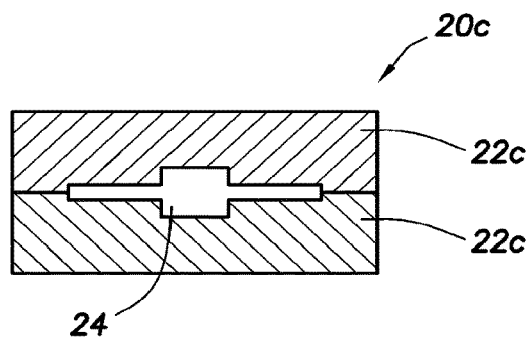
FIG. 2C shows a miniature ingestible device with a film in accordance with one aspect of the present invention.

Referring now to FIG. 2C, in accordance with another aspect of the present invention an MID 20c is shown with a film material 22c surrounding the IEM 24. In accordance with another aspect of the present invention, the film material 22c disintegrate upon contact with fluid. The film material 22c may be made of and includes the following examples: at least one of polyethylene oxide and hydroxypropyl cellulose with a plasticizer comprising at least one of triethylcitrate, glycerol, dibutyl sebacate, and polyethylene glycol.

Figure 2D:
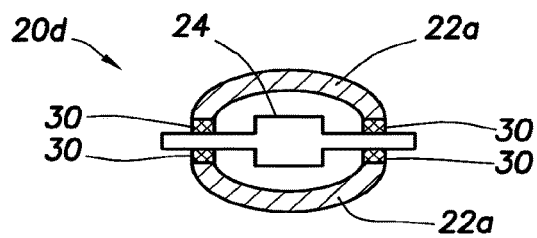
FIG. 2D shows a miniature ingestible device with a powder glued to an ingestible device in accordance with one aspect of the present invention.

Referring now to FIG. 2D, an MID 20d in shown with an excipient material 22a in a preformed shape. The excipient material 22a is glued or laminated onto the IEM 24 using a material 30. The material 30 may be a liquid adhesive or a dry adhesive that is pressure sensitive. The excipient material 22a is shown in a dome like shape with an air gap between the excipient material 22a and the IEM 24. However, the scope of the present invention is not limited by the shape of the excipient material 22a or the distance separating the excipient material 22a from the IEM 24. In accordance with other aspects of the present invention, the excipient material 22a may be shaped to fit the dimension of the IEM 24 exactly on the inner surface and maintain a dome or convex shape on the exterior. This is helpful in the handling and assembly process of the MID 20d into the capsule, such as shown in FIG. 1 given that many of the pharmaceutical manufacturing facilities are designed to handle convex shaped objects.

Figure 2E:
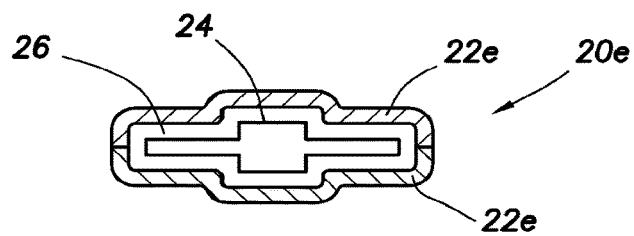
FIG. 2E shows a miniature ingestible device with a film in accordance with one aspect of the present invention.

Referring now to FIG. 2E, an MID 20e includes a film 22e surrounding the IEM 24. The MID 20e is shown with a gap 26 separating the IEM 24 from film 22e. The scope of the present invention is not limited by the type of material used to make the film 22e. The film 22e is similar to the film 32 of FIG. 2B and may be made of any suitable material, including but not limited to: of polyethylene oxide and hydroxypropyl cellulose with a plasticizer comprising at least one of triethylcitrate, glycerol, dibutyl sebacate, and polyethylene glycol. The scope of the present invention is not limited by the size of the gap 26. In accordance with another aspect of the present invention, the gap 26 may be minimal so that portions of the film 22e are in contact with the IEM 24. In accordance with another aspect of the present invention, the gap 26 may be filled with a material or a drug as appropriate.

Figure 2F:
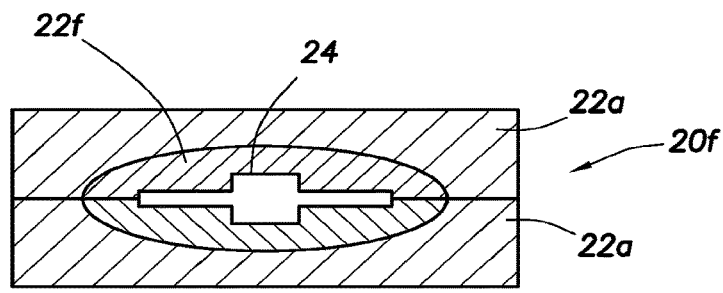
FIG. 2F shows a miniature ingestible device with a film surrounded by a powder in accordance with one aspect of the present invention.

Referring now to FIG. 2F, an MID 20f is shown with an IEM 24 surrounded by a film 22f. The film 22f is surrounded by the excipient material 22a. As shown, the film 22f is in direct contact with the IEM 24 and surrounds the IEM 24. Furthermore, the MID 20f is shown with the excipient material 22a surrounding and in contact with the film 22f.

In accordance with the teaching of the present invention, the shape of the various MIDs 20 shown through FIGS. 2A, 2B, 2C, 2D, 2E, and 2F as illustrative and not intended as a limitation. For example, the shape of the MID 24, in accordance with various aspects of the present invention, may be oval or rectangular or something in between, for example, vertical sides and convex top and bottom.

Referring now to FIGS. 3, 4, and 5, a capsule 10 is shown with an MID 20. There may be other materials, including pharmaceutical material or drugs or active agents, inside the capsule 10. However, for the purpose of demonstrating the designation steps of the capsule and the MID 20, only these two elements are shown. In FIG. 3 the capsule 10 is shown when it is stored and not in contact with fluid. Once the capsule 10 comes into contact with fluid, the capsule 10 begins to disintegrate and the walls of the capsule 10 start to collapse to become capsule 10a. Fluid AA enters the cavity defined by the capsule 10a. As such, fluid BB comes into contact with MID 20. In accordance with one aspect of the present invention, the excipient material of the MID 20 begins to dissolve and expand and the MID 20 starts to lose its shape and becomes the MID 40. As shown in FIG. 5, at a more advanced stage with longer contact with the fluid AA that entered the capsule 10, the capsule 10 is shown with the walls falling apart and collapsing as capsule pieces 10b. The fluid advances to contact the MID 20 as fluid BB to resulting in further expansion and disintegration of MID 20, which is shown as MID 50.

Referring now to FIG. 6, a process for creating an MID, in accordance with one aspect of the present invention, includes loading an excipient material 60a into a press 62. The mass of the excipient material 60a used is in the order of 0.045 g of powder material. However, the scope of the present invention is not limited by amount of material used. The IEM 24 is placed in the press 62. Then additional excipient material 60b, similar in mass to the amount of excipient material 60a, is added into the press 62 and on top of the IEM 24. Then a plunger 64 is used to apply pressure and assemble the materials into the MID, such as the MID 20a of FIG. 1. The pressure used to assemble the MID varies and the scope of the present invention is not limited thereby. Industry standard combined with the tolerances for the amount of pressure that can be applied the IEM 24 are the deciding factors. In accordance with one aspect of the present invention, typical pressures are in the order of 1000 psi.

Referring now to FIG. 7, a process for creating an MID, in accordance with one aspect of the present invention, includes placing a film material 70 on a press table 72. The IEM 24 is placed on top of the film material 70 and another sheet of film material 70 is place on top of the IEM 24. The film material 70 is sized such that edges 70a, 70b, 70c, and 70d extend beyond the edges of the IEM 24. Then a thermal plunger 74 is used to apply pressure and heat to the film material 70 such that the edges 70a and 70b are laminated or secured together. Similarly, the edges 70c and 70d are laminated together.

Referring now to FIG. 8, a process for creating an MID, in accordance with one aspect of the present invention, includes placing a film material 80 on a press table 82. An internal MID 20, such as the one created by the process shown in FIG. 6, is placed on top of the film material 80 and another sheet of film material 80 is place on top of the internal MID 20. The film material 80 is sized such that edges 80a, 80b, 80c, and 80d extend beyond the edges of the internal MID 20. Then a thermal plunger 84 is used to apply pressure and heat to the film material 80 such that the edges 80a and 80b are laminated or secured together. Similarly, the edges 80c and 80d are laminated together.

Figure 9:
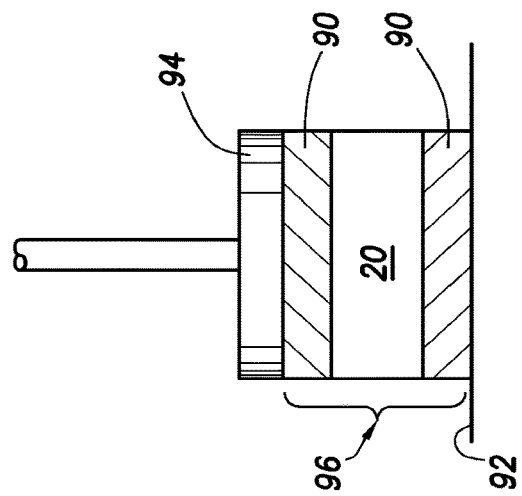
FIG. 9 shows an assembly unit for creating a miniature ingestible device in accordance with the present invention.

Referring now to FIG. 9, the process for creating an MID 96, such as the MID 20b of FIG. 2B, includes the process of placing a film material 90, similar to the film material disclosed throughout the present invention, on a press table 92, similar to the press table 72 of FIG. 7. Then a second film 90 is placed on top of the MID 20. Then a thermal plunger 94 is used to apply pressure and heat to the film materials 90 to secure the film material to the top and bottom of the MID 20, which results in the MID 96 with the side edges exposed.

Figure 10:
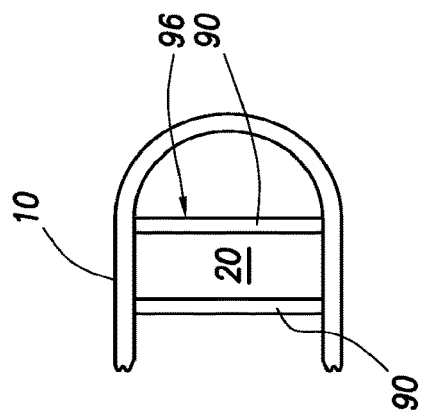
FIG. 10 shows one end of a capsule with a miniature ingestible device.

Referring now to FIG. 10, the MID 96 of FIG. 9 is placed within one end of the capsule 10, such as the capsule 10 of FIG. 1, in accordance with one aspect of the present invention. The MID 96, includes film materials 90 that do not dissolve or are not soluble. As such, when the fluid comes into contact with the MID 20, the MID 20 expands and breaks apart the walls of the capsule 10 to further ensure separation of the IEM 24, which is within the MID 20, from the capsule material.

Figure 11:
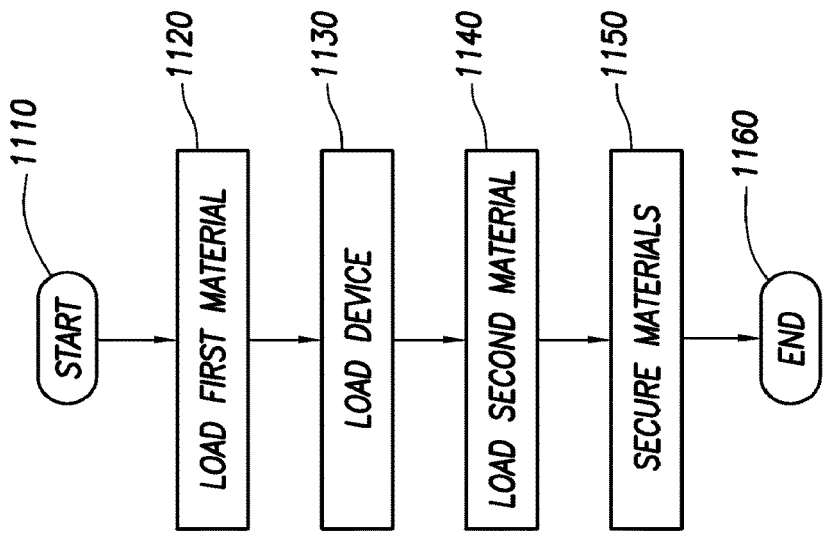
FIG. 11 is a flow process for manufacturing a miniature ingestible device.

Referring now to FIG. 11, the process for manufacturing or assembling the MID, such as the MID 20, in accordance with the present invention begin at step 1110. At step 1120 the first material is added to the assembly unit. As noted above the first material may be in powder form or a film material and loaded into a press on placed on a press table, respectively. At step 1130, the device, such as the IEM, is loaded into the assembly unit. At step 1140 a second material is added. At step 1150 the assembly in completed by securing the materials and the device to form the MID. As noted above, securing may be done with pressure, thermal, or glue materials. The scope of the present invention is not limited by the approach used to secure and produce the MID.

As noted above, the film material may be made of a variety of materials or films, such as polymer films that include polyethylene oxide, hydroxyprpyl cellulose, and triethyl citrate. Other films that can be used include any solulable polymer, plasticizer. The film material, in accordance with one aspect of the present invention, provides a moisture barrier and dissolves under the proper conditions to delay activation of the IEM or device. The film layer is designed to provide sufficient delay in exposure of the device to the surrounding fluids relative to the disintegration and dispersion of the capsule material and the content of the capsule. The film layer may includes the soluble materials, barrier materials (such as lipids, polyvinyl alcohol), processing aids (such as plasticizers, adhesion promoters), and stabilizers. Furthermore, the film may be manufactured via lamination, application of a coating solution or slurry followed by a cure. In accordance with other aspects of the present invention, the film or layer may be formed using dry compression, such as a tablet press.

There are a variety of active agents or pharmaceutical products that can be placed inside of a capsule. For example, there are FDA approved drugs, drugs that are disclosed chemically in a patent application or in an issued patent, there are drugs are disclosed in the Orange Book as part of the approved drug products, and generics. In accordance with the teachings of the present inventions, any one or combination of such drugs may be placed within the capsule along with the device. Each of those drugs may have a specific and unique impact on the operation of the device as well as the disintegration of the film used because of the unique chemical composition. As such, the type of material uses as the film material may vary to be compatible to the chemical composition of the products used. Thus, the scope of the present invention is not limited by the type of content of the capsule and the film or coating layer around the electronic components of the device.

In accordance with another aspect and benefit of the present invention, the film or coating will also prevent the interaction components of the device with the drug inside the capsule and as such the device will not alter or impact the effectiveness of the drug.

As noted above various disintegration materials may be used to surround the electronic components. For example, a disintegrant may be sodium starch glycolate or a water soluble excipient such as hydroxypropyl cellulose. It will also be apparent that the various layers disclosed can be eliminated or combined depending on the material employed and the properties thereof.

As described herein, the term "ingested" or "ingest" or "ingesting" is understood to mean any introduction of the system internal to the in-vivo. For example, ingesting includes simply placing the product in the mouth all the way to the descending colon. Thus, the term ingesting refers to any instant in time when the system is introduced to an environment that contains a conducting fluid. Another example would be a situation when a non-conducting fluid is mixed with a conducting fluid. In such a situation the MID would be present in the non-conduction fluid and when the two fluids are mixed, the system comes into contact with the conducting fluid and the IEM within the MID is activated. Yet another example would be the situation when the presence of certain conducting fluids needed to be detected. In such instances, the presence of the system, which would be activated, within the conducting fluid, could be detected and, hence, the presence of the respective fluid would be detected.

According to another aspect embodiments of the invention may defined in at least one of the following clauses.

Clause 1: A device for placement within a capsule, comprising:
  an ingestible element; and
  a material in physical communication with at least part of the ingestible element, wherein the material facilitates physical separation of the ingestible element from at least a portion of the capsule during a disintegration.

Clause 2: The device of clause 1, wherein the ingestible unit comprises an ingestible event marker.

Clause 3: The device of clause 1 or 2, wherein the material comprises a disintegrant and comprises at least one of povidone, crospovidone,
  croscarmellose sodium, sodium starch glycolate, starrtch, and microcrystalline cellulose cellulose.

Clause 4: The device of clause 3, wherein the super-disintegrant is physically coupled to the ingestible unit using pressure.

Clause 5: The device of clause 3, wherein the super-disintegrant is physically coupled to the ingestible unit using an adhesive material.

Clause 6: The device of any of the preceding clauses, wherein the material includes a soluble film material that comprises at least one of polyethylene oxide and hydroxypropyl cellulose with a plasticizer comprising at least one of triethylcitrate, glycerol, dibutyl sebacate, and polyethylene glycol.

Clause 7: The device of any of the preceding clauses, wherein the film material is physically coupled to the ingestible unit using thermal application.

Clause 8: A unit including a pharmaceutical product, wherein the unit is ingestible and activated upon contact with a fluid, the unit comprising:
  a capsule including a wall, wherein the capsule defines a cavity for holding the pharmaceutical product and wherein the wall loses its shape and disintegrates upon contact with the fluid; and
  a device, preferably a device according to any of the preceding clauses, the device including a partial power source located within the cavity of the capsule, wherein the device is capable of encoding information in a current flow, which occurs when the device is activated as the partial power source contacts the fluid, the device further comprising:
    a first surface with a first portion of the partial power source;
    a second surface with a second portion of the partial power source; and
    a control unit for encoding the information in the current flow, wherein the control unit is electrically coupled between the first and second portions of the partial power source; and
  a material positioned over the first portion and the second portion of the partial power source, wherein the material disintegrates upon contact with the fluid to provide physical separation between the device and the disintegrating wall of the capsule.

Clause 9: The unit of clause 8, wherein the material surrounds the device and is secured to itself to define a cavity between the material and the device.

Clause 10: A system for tracking delivery of a pharmaceutical agent, the system comprising:
  a capsule defining a cavity;
  miniature ingestible tablet located in the cavity of the capsule, the miniature ingestible tablet comprising:
    an ingestible device according to any of clauses 1-7, preferably a device in a unit according to any of clauses 8-9, the device being activated upon contact with a fluid and comprising an ingestible element and a tablet material in physical communication with at least part of the ingestible device; and
    a material at least partially surrounding the miniature ingestible tablet, wherein the tablet material facilitates physical separation of the ingestible device from at least a portion of the capsule during a disintegration process.

Clause 11: The system of clause 10, wherein the material and/or the tablet material is a soluble film material that includes at least one of polyethylene oxide and hydroxypropyl cellulose with a plasticizer comprising at least one of triethylcitrate, glycerol, dibutyl sebacate, and polyethylene glycol.

Clause 12: The system of clause 11, wherein the material is a non-soluble film material that defines an opening at either end of the miniature ingestible tablet such that when the tablet material comes in contact with the fluid and expands the film material controls the direction of expansion.

Clause 13: The system of clause 11 or 12, wherein the film material delays contact between the fluid and the ingestible device to delay activation.

Clause 14: A method of manufacturing a device, preferably for assembly into a pharmaceutical product to prevent damage to the device and allow for handling and manipulation of the device during assembly and for reliable activation of the device upon ingestion of the pharmaceutical product, the method comprising the steps of:
    providing a first layer of material;
    positioning the device including a first portion and a second portion, wherein the first portion of the device is in contact with the first layer of material;
    providing a second layer of material, wherein the second layer of material is in contact with the second portion of the device; and
    securing the first and second material to the device to produce a miniature ingestible marker.

Clause 15: The method of clause 14, further comprising the step of physically associating the miniature ingestible marker with the pharmaceutical product, wherein physically associating the miniature ingestible marker with the pharmaceutical product comprises incorporating the miniature ingestible marker in a gelatin capsule.

Clause 16: The method according to clause 14 or 15, wherein the device is a device according to any of clauses 1-7.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A manufacturing process comprising:
    loading a first portion of a tablet material into a press, the tablet material formulated to disintegrate upon contact with a fluid;
    loading an ingestible event marker into the press adjacent to the first portion of the tablet material, the ingestible event marker comprising:
        a partial power source having a first portion and a second portion and configured to generate power upon contact of the first portion and the second portion with the fluid; and
        a control unit electrically coupled between the first portion and the second portion of the partial power source, wherein the control unit is configured to be activated by receiving the power from the partial power source and to encode information in a current flow between the first portion and the second portion through the fluid;
    loading a second portion of the tablet material into the press on a side positioned opposite of the ingestible event marker from the first portion of the tablet material, such that the ingestible event marker resides in the press between the first portion and the second portion of the tablet material;
    applying pressure in the press to the first and the second portions of the tablet material, such that the first portion and the second portion of the tablet material completely encapsulates the ingestible event marker and the first portion and the second portion of the partial power source are exposed after the first portion and the second portion of the tablet material disintegrates upon contact with the fluid; and
    covering at least partially the first portion and the second portion of the tablet material with a non-soluble film material to form an ingestible device, wherein the film material is formulated and configured to inhibit interaction between the tablet material and a pharmaceutical product during disintegration of the pharmaceutical product; and
    wherein the film material covers at least partially the first portion and the second portion of the tablet material such that when the first portion and the second portion of the tablet material come in contact with the fluid, the film material controls the direction of expansion of the tablet material as the tablet material expands.

2. The process of claim 1, further comprising enveloping the ingestible device with a capsule, wherein the first portion and the second portion of the tablet material further isolate the first portion and the second portion of the partial power source and the control unit from the capsule.

3. The process of claim 2, wherein the capsule comprises a wall defining a cavity for containing the ingestible device, the wall configured to lose its shape and disintegrate upon contact with the fluid.

4. The process of claim 3, further comprising filling the cavity with the pharmaceutical product.

5. The process of claim 1, wherein the tablet material comprises an excipient material that is a disintegrant and comprises at least one of; povidone, crospovidone, croscarmellose sodium, sodium starch glycolate, starch, or microcrystalline cellulose.

6. The process of claim 1, wherein the tablet material is a soluble film material that comprises at least one of polyethylene oxide or hydroxypropyl cellulose.

* * * * *